United States Patent
Sandor et al.

(10) Patent No.: US 10,353,032 B2
(45) Date of Patent: **\*Jul. 16, 2019**

(54) VISCOSITY DETERMINATION APPARATUS, SYSTEMS, AND METHODS

(71) Applicant: HALLIBURTON ENERGY SERVICES, INC., Houston, TX (US)

(72) Inventors: Magdalena Traico Sandor, Humble, TX (US); Songhua Chen, Katy, TX (US)

(73) Assignee: HALLIBURTON ENERGY SERVICES, INC., Houston, TX (US)

( \* ) Notice: Subject to any disclaimer, the term of this patent is extended or adjusted under 35 U.S.C. 154(b) by 0 days.

This patent is subject to a terminal disclaimer.

(21) Appl. No.: 15/516,652

(22) PCT Filed: Oct. 27, 2015

(86) PCT No.: PCT/US2015/057597
§ 371 (c)(1),
(2) Date: Apr. 3, 2017

(87) PCT Pub. No.: WO2017/074316
PCT Pub. Date: May 4, 2017

(65) Prior Publication Data
US 2018/0231625 A1 Aug. 16, 2018

(51) Int. Cl.
*G01R 33/44* (2006.01)
*G01R 33/561* (2006.01)
*G01V 3/32* (2006.01)
*G01N 24/08* (2006.01)
*E21B 47/10* (2012.01)

(52) U.S. Cl.
CPC ............ *G01R 33/448* (2013.01); *E21B 47/10* (2013.01); *G01N 24/081* (2013.01); *G01R 33/5615* (2013.01); *G01V 3/32* (2013.01)

(58) Field of Classification Search
USPC .......................... 324/300–322; 600/407–435
See application file for complete search history.

(56) References Cited

U.S. PATENT DOCUMENTS

| | | | | |
|---|---|---|---|---|
| 6,825,657 B2 * | 11/2004 | Kleinberg | ............ | G01N 24/081 324/303 |
| 7,538,129 B2 * | 5/2009 | Harran | ................. | C07D 498/22 514/366 |
| 2003/0006768 A1 * | 1/2003 | Kleinberg | ............ | G01N 24/081 324/303 |
| 2004/0041562 A1 | 3/2004 | Speier | | |

(Continued)

OTHER PUBLICATIONS

Korean Intellectual Property Office, International Search Report and Written Opinion, dated Jul. 27, 2016, 14 pages, Korea.

(Continued)

*Primary Examiner* — Melissa J Koval
*Assistant Examiner* — Tiffany A Fetzner

(57) ABSTRACT

In some embodiments, an apparatus and a system, as well as a method and article of manufacture, may operate to measure nuclear magnetic resonance relaxation times in a fluid. Further activity may include determining a viscosity of the fluid based on at least one ratio of the relaxation times, and operating a controlled device based on the viscosity. Additional apparatus, systems, and methods are disclosed.

19 Claims, 6 Drawing Sheets

(56) References Cited

U.S. PATENT DOCUMENTS

| | | | |
|---|---|---|---|
| 2007/0149583 A1* | 6/2007 | Harran | C07D 498/22 |
| | | | 514/375 |
| 2008/0272773 A1 | 11/2008 | Romero et al. | |
| 2009/0093962 A1 | 4/2009 | Akkurt | |
| 2009/0289628 A1 | 11/2009 | Cao Minh | |
| 2016/0108556 A1* | 4/2016 | Vlasblom | C08K 5/3435 |
| | | | 428/36.9 |
| 2016/0169839 A1* | 6/2016 | Gottlieb | G01N 29/02 |
| | | | 367/7 |
| 2018/0017699 A1* | 1/2018 | Sandor | G01V 3/14 |
| 2018/0231625 A1* | 8/2018 | Sandor | E21B 47/10 |

OTHER PUBLICATIONS

Christian Straley, Dan Rossini, Harold Vinegar and Chris Morriss, Core Analysis by Low Field NMR, 1994, 14 pages, SCA-9404.

G.A.Latorraca, S.W.Stonard, P.R. Webber, R.M. Carlson and K.J. Dunn, Heavy Oil Viscosity Determination Using NMR Logs, May 30-Jun. 3 1999, 11 pages, SPWLA $40^{th}$ Annual Logging Symposium.

R.L. Kleinberg and H.J. Vinegar, NMR Properties of Reservoir Fluids, Nov.-Dec. 1996, 13 pages, The Log Analyst.

* cited by examiner

VISCOSITY DETERMINATION APPARATUS, SYSTEMS, AND METHODS

CROSS-REFERENCE TO RELATED APPLICATIONS

This application is a U.S. national stage patent application of International Patent Application No. PCT/US2015/057597, filed on Oct. 27, 2015 the benefit of which is claimed and the disclosure of which is incorporated herein by reference in its entirety.

BACKGROUND

Understanding the structure and properties of geological formations can reduce the cost of drilling wells for oil and gas exploration. Measurements made in a borehole (i.e., downhole measurements) are typically performed to attain this understanding, to identify the composition and distribution of material that surrounds the measurement device downhole. For example, it is often useful to determine the viscosity of formation fluids, including those that occupy pore space in the formation, since the knowledge of whether light or heavy oils are present can influence the course of oil field production operations.

DETAILED DESCRIPTION

To address some of the challenges noted above, as well as others, various embodiments may operate to provide predictions of heavy oil viscosity. Wireline and/or logging while drilling (LWD) operations that provide NMR spin-lattice relaxation time ($T_1$), spin-spin relaxation time ($T_2$), and echo spacing time (TE) information can be used.

To begin, it is useful to note that the value of $T_1$ and $T_2$ relaxation times depend on molecular motion, which is related to the size distribution of molecules, as well as their intermolecular and intramolecular interactions. For heavy oils, significant contributions to the relaxation behavior come from heavy components, such as asphaltenes and resins, which give rise to a substantially exponential increase in viscosity with a minor increase in concentration. Moreover, in heavy oils, intramolecular dipole-dipole interactions govern the relationship between $T_1$ and $T_2$ relaxation times, and correlation time (the time it takes an average molecule to rotate one radian). When Brownian motion is assumed, it has been observed that this relationship can be used to determine measurable quantities, such as rotational diffusivity and viscosity.

$T_1$ and $T_2$ relaxation rates can be characterized by the following equations:

$$\frac{1}{T_1} = \frac{9}{20}\left(\frac{\mu_o}{4\pi}\right)^2 \frac{\hbar^2 \gamma^4}{r^6} \tau_c \left[\frac{2/3}{1+(\omega_o\tau_c)^2} + \frac{8/3}{1+(2\omega_o\tau_c)^2}\right] \text{ and}$$

$$\frac{1}{T_2} = \frac{9}{20}\left(\frac{\mu_o}{4\pi}\right)^2 \frac{\hbar^2 \gamma^4}{r^6} \tau_c \left[1 + \frac{5/3}{1+(\omega_o\tau_c)^2} + \frac{2/3}{1+(2\omega_o\tau_c)^2}\right],$$

where $\tau_C$ is the correlation time, $\omega_o$ is the Larmor frequency, $\mu_o$ is the magnetic permeability, $\hbar$ is Plank's constant, $\gamma$ is the gyromagnetic ratio constant, and r is the distance to nearest protons.

Figure 1:
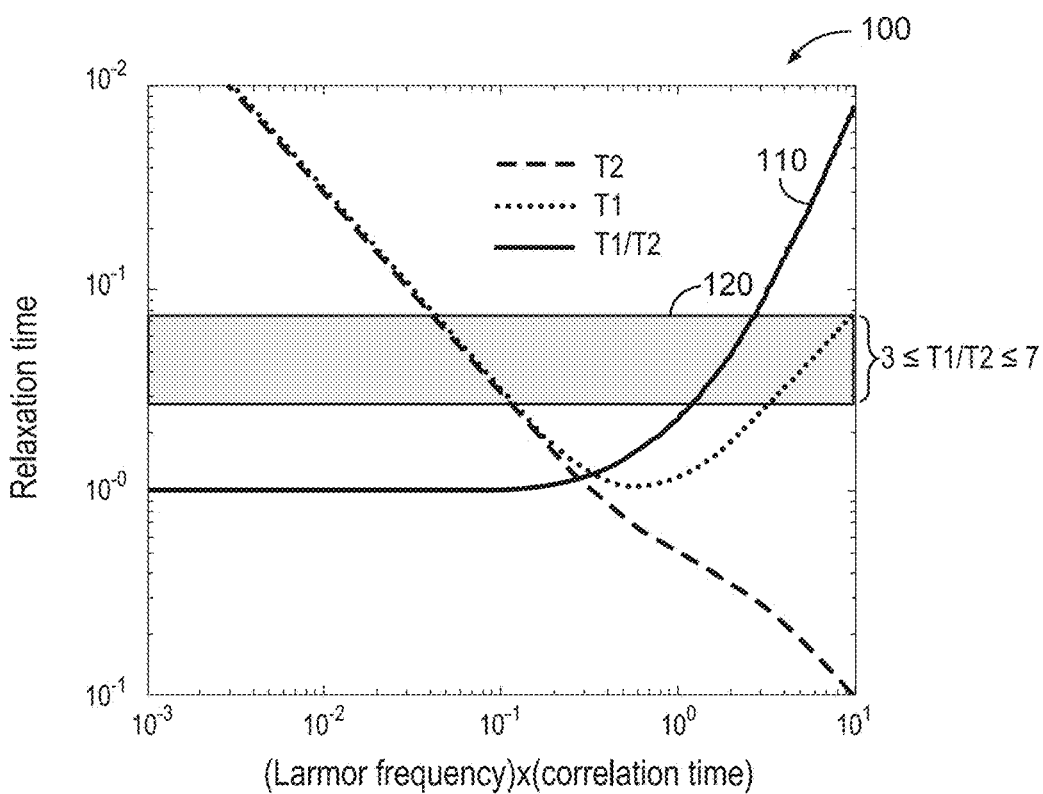
FIG. 1 is a graph illustrating the theoretical relationship between nuclear magnetic resonance (NMR) spin-spin relaxation times ($T_2$), spin-lattice relaxation times ($T_1$), and $T_1/T_2$ ratios for fluid/solids, versus the Larmor frequency multiplied by the correlation time, according to various embodiments.

FIG. 1 is a graph illustrating the theoretical relationship between nuclear magnetic resonance (NMR) spin-spin relaxation times ($T_2$), spin-lattice relaxation times ($T_1$), and $T_1/T_2$ ratios for fluid/solids, versus the Larmor frequency multiplied by the correlation time, according to various embodiments. As will be explained in more detail below, the graph 100 clearly demonstrates a sensitive relationship between viscosity and NMR relaxation time as TE varies.

For light oils or high temperature conditions, the extreme narrowing approximation is valid where short correlation times are present. Under the assumption of a fast motion limit, where the molecular motions average out the dipole-dipole interactions, the $T_1$ and $T_2$ relaxation times are related to the rheological viscosity η land thermal energy according to the equation:

$$\frac{1}{T_1} = \frac{1}{T_2} \sim \eta/kT,$$

where k is the Boltzmann constant, and T is the absolute temperature in Kelvin.

In FIG. 1, the proportionality between the $T_1$ and $T_2$ relaxation time and viscosity can be noted at shorter values of correlations time. Although this functional form is often implemented in the development of NMR heavy oil correlations, it is conceptually inappropriate since heavy crudes are inherently complex and can be affected by non-Debye relaxation activity.

FIG. 1 also demonstrates the dependence of the ratio of relaxation times $T_1/T_2$, shown as the curve 110 As expected, for light crude oils, the value of the ratio is approximately one, and substantially independent of viscosity. As viscosity increases, and motional narrowing is no longer satisfied, the sensitivity of the $T_1/T_2$ ratio curve 110 increases. The highlighted region 120, indicating a range of $T_1/T_2$ ratio values of about three to about seven, represents a laboratory-sampled region for heavy oils that have API gravities ranging from 10 to 14. Of course, various embodiments are not to be so limited; in some embodiments, the ratio of $T_1/T_2$ ranges from about 1 to about 20, and more.

Thus, the curve 110 can be used to indicate heavy oil zones of a particular range of viscosities and also identify light oil intervals or pay zones where the ratio $T_1/T_2$ is approximately equal to one. For longer correlations times or when the ratio $T_1/T_2$ rises above a value of two or three, there is an approximately linear relationship between the ratio $T_1/T_2$ and viscosity. This relationship provides a practical way to use measured $T_1$ and $T_2$ relaxation time information to infer the viscosity of heavy crudes.

Figure 2:
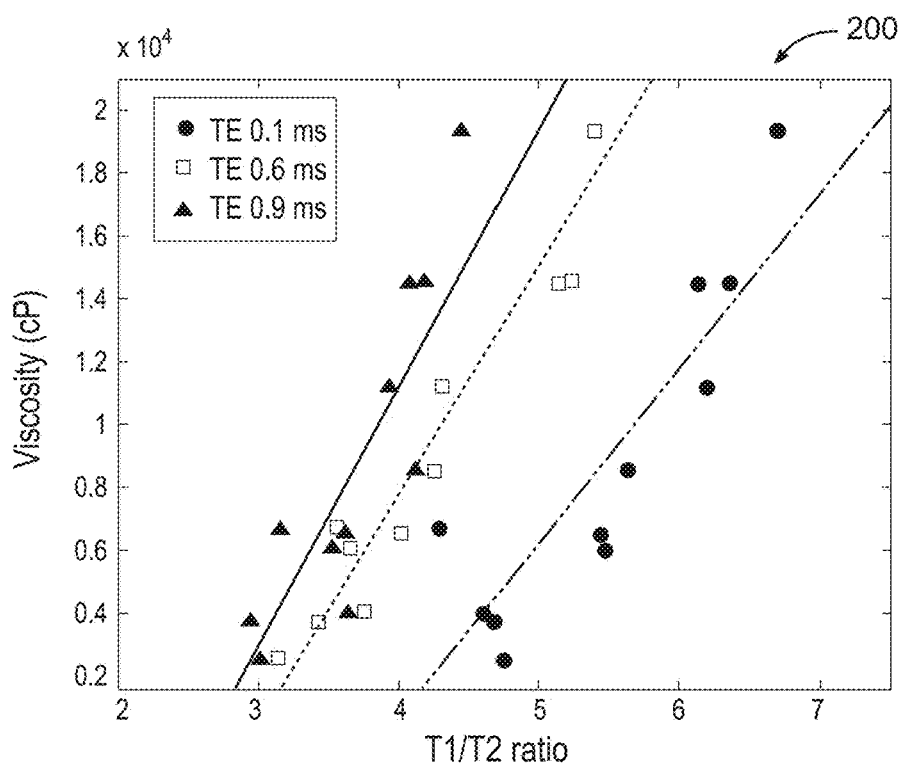
FIG. 2 is a graph illustrating viscosity versus the ratio of relaxation times ($T_1/T_2$) over a range of echo spacing time (TE) values, according to various embodiments.

FIG. 2 is a graph illustrating viscosity versus the ratio of relaxation times ($T_1/T_2$) over a range of echo spacing time (TE) values, according to various embodiments. Here viscosity versus the $T_1/T_2$ ratio of several heavy crude oil samples, ranging in API gravity from 10-14 as a function of TE values of 0.1 ms, 0.6 ms, and 0.9 ms is shown. The horizontal axis records the results captured by the highlighted region 120 in FIG. 1. Since the distribution of $T_1$ and $T_2$ relaxation times for heavy oils is very broad, the geometric mean for each distribution was determined to compute the $T_1/T_2$ ratio. A systematic shift of the $T_1/T_2$ ratio with echo spacing is expected, since longer dead times result in larger signal loss when relaxation times are relatively short. Therefore, over a range of $T_1/T_2$ ratio values of about two to about ten in some embodiments, and about three to about seven in some embodiments, the relationship between the viscosity and $T_1/T_2$ ratio can be expressed as Equation (1):

$$\eta = (aTE+c)(T_1/T_2)+b, \quad (1)$$

where $\eta$ is the rheological viscosity; $T_1/T_2$ is the ratio obtained from the geometric mean of the distributions for $T_1$ and $T_2$ relaxation times; TE is the echo spacing time; and a, b, and c are fitting coefficients obtained from linear regression analysis. The data demonstrates the substantially linear relationship between viscosity and the $T_1/T_2$ ratio, as well as systematic changes corresponding to TE, which is useful in the adaptation of the relationship to logging situations where there are constraints on the values of TE that can be achieved. The sensitivity of the relationship between viscosity and the $T_1/T_2$ ratio is suggested from the slope, which is proportional to TE and becomes especially advantageous at greater values of TE.

Figure 3:
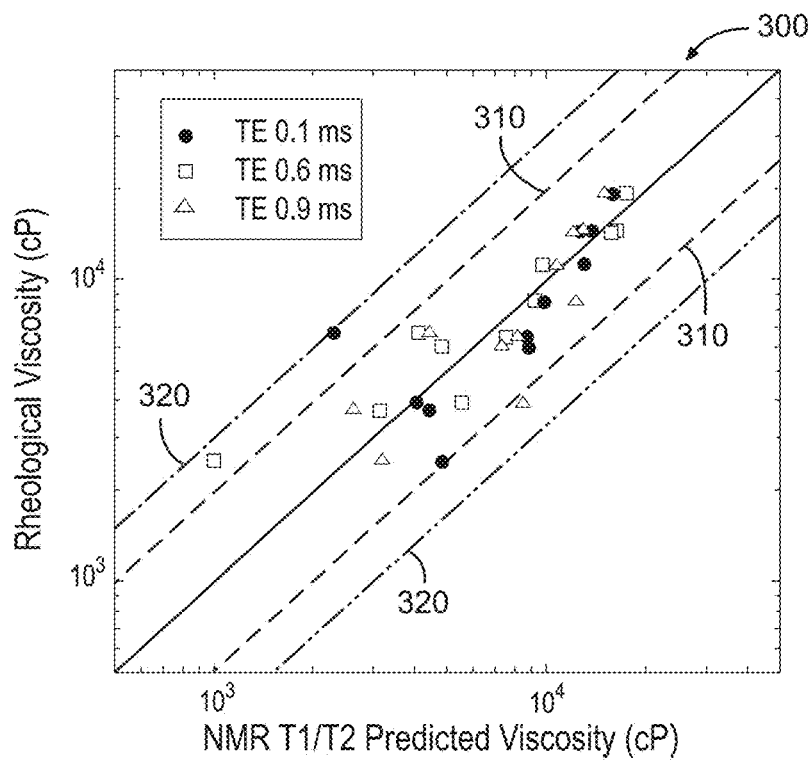
FIG. 3 is a graph comparing rheological viscosity and predicted viscosity as a function of the echo time, according to various embodiments.

FIG. 3 is a graph 300 comparing rheological viscosity and predicted viscosity as a function of the echo time, according to various embodiments. Here the rheological and NMR predicted viscosities are compared as a function of TE values of 0.1 ms, 0.6 ms, and 0.9 ms; these are the same values used in FIG. 2. The graph 300 demonstrates that the correlation approach yields NMR predicted viscosities that mostly fall within a factor of two (channel 310) or three (channel 320) of a line drawn to represent a 1:1 correspondence between predicted and actual measured viscosities.

To improve the robustness of the heavy oil viscosity correlation prediction, the correlation can be reevaluated in such manner that a multitude of NMR experiments over a range of TE values are acquired, processed to obtain $T_1/T_2$ ratio values, and then averaged. This can be accomplished once a preliminary correlation is built from Equation (1), where the values of coefficients a, b, and c are determined. The correlation can then be expressed in the form:

$$Y = \eta - b = \sum_{i=1}^{n} A_i \cdot R_i / n,$$

where $A_i = a \cdot TE_i + c$, $R_i = T_1/T_2$, and n is the index for TE. Here Y is a simplified representation of the correlation, as a viscosity computed from an average of $T_1/T_2$ ratios taking into account experimental parameters and fitting coefficients—the experimental uncertainties (noise, temperature gradient in sample, sample impurities, etc.) that may contribute to scatter in predicted versus rheological viscosities (e.g, as shown in FIG. 3). Taking an average may counteract these fluctuations and yield a viscosity that is closer to the measured viscosity. Thus, given that experimental uncertainties contribute to $A_i \cdot R_i$, implementing this approach is expected to counteract fluctuations of the viscosity prediction.

Figure 4:
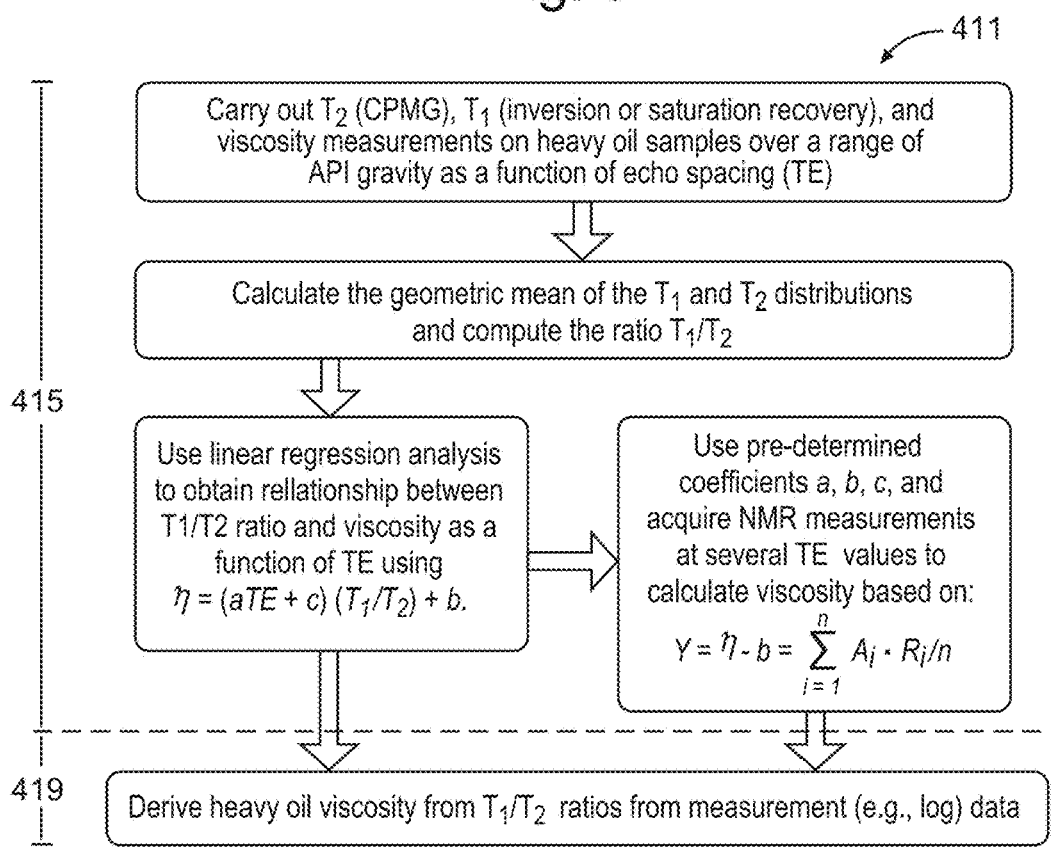
FIG. 4 is a flow diagram of a method that can be used to determine fluid viscosity using measured relaxations times, according to various embodiments.

FIG. 4 is a flow diagram of a method 411 that can be used to determine fluid viscosity using measured relaxations times, according to various embodiments. The method 411 illustrated in FIG. 4 summarizes the workflow described previously, separating the activity of viscosity determination into two aspects 415, 419. In the first aspect 415, a correlation between oil viscosity and the NMR $T_1/T_2$ ratio is derived. This aspect 415 makes use of NMR measurements and independent viscosity measurements to establish the correlation.

The second aspect 419 applies the correlation determined in the first aspect 415 to NMR measurement data (e.g., lab, core, or log data), enabling the determination of viscosity, based on lab or field measurements of $T_1$ and $T_2$ relaxation times, and TE values for samples, wells, or reservoirs of interest. Thus, additional embodiments may be realized.

Figure 5:
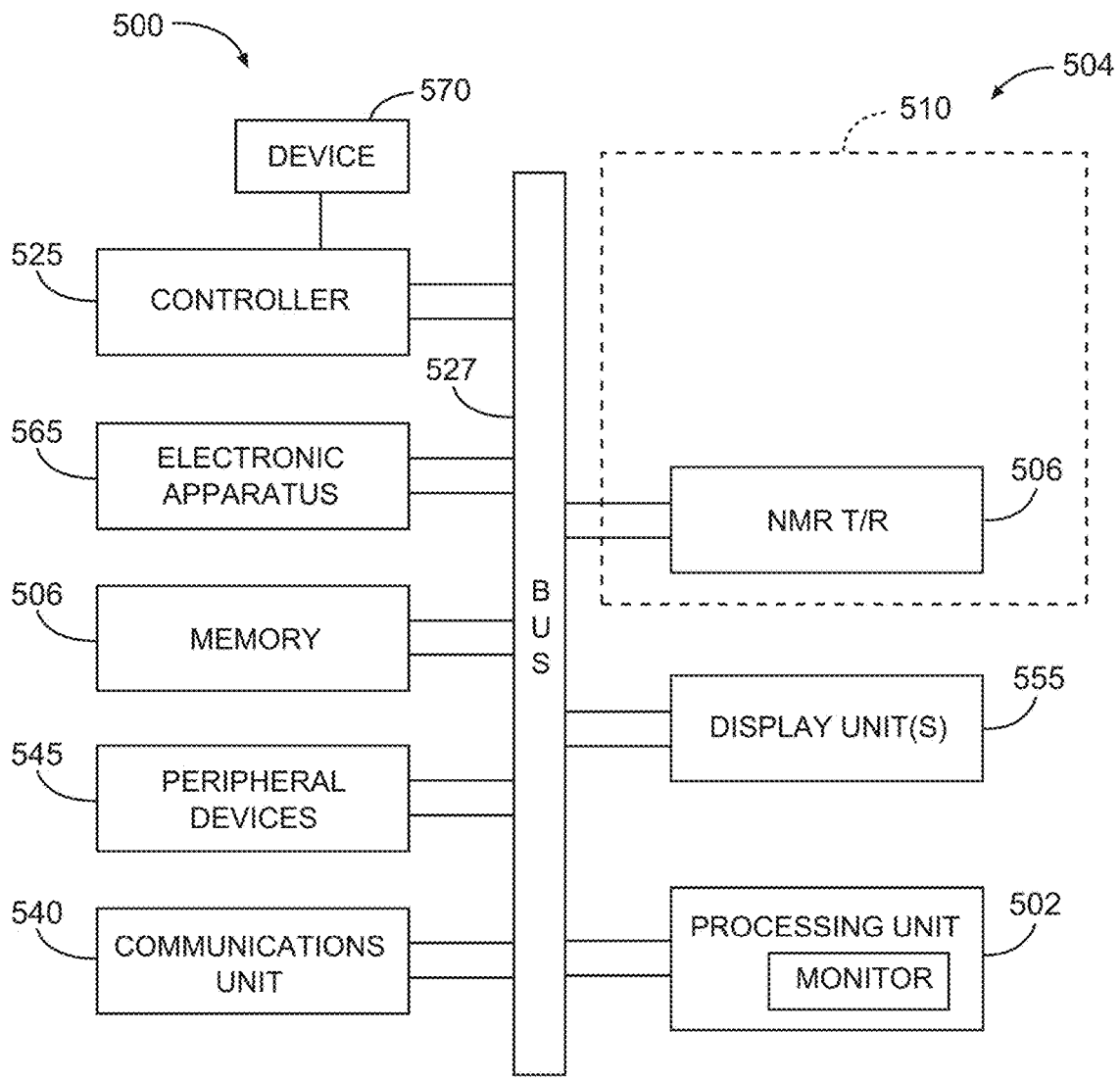
FIG. 5 is a block diagram of a data acquisition, processing, and control system according to various embodiments.

For example, FIG. 5 is a block diagram of a data acquisition, processing, and control system 500 according to various embodiments. Here it can be seen that the system 500 may further include one or more transmitters and/or receivers, such as NMR transmitters receivers 506 as part of a measurement device 504. When configured in this manner, the logging system 500 can receive measurements and other data (e.g., location, relaxation time, and TE information) from the NMR transmitters/receivers 506. The device 504 can be located on the surface of the Earth, such as in a laboratory, or downhole, perhaps attached to a housing 510.

The processing unit 502 can couple to the measurement device 504 to obtain measurements from the measurement device 504, and its components. Thus, in some embodiments, a system 500, such as a logging system, comprises a housing 510 that forms part of the device 504, and other elements. The housing 510 might take the form of a wireline tool body, or a downhole tool as described in more detail below with reference to FIGS. 7 and 8. The processing unit 502 may be part of a surface workstation or attached to a downhole tool housing. In some embodiments, the processing unit 502 is packaged within the housing 510.

The system 500 can include a controller 525, other electronic apparatus 565, and a communications unit 540. The controller 525 and the processing unit 502 can be fabricated to operate the measurement device 504 to acquire measurement data, such as signals representing NMR sensor measurements.

The controller 525 may operate to control a controlled device 570, either directly, or using commands from the processing unit 502. The controlled device might take the form of a pump in some embodiments, to directly control the pumping rate, or draw-down pressure. In some embodiments, the controlled device 570 might take the form of an alarm, to be activated in response to the activity of a monitoring element MONITOR that is used to observe the current $T_1/T_2$ ratio, and the TE value, and compare the predicted viscosities with values previously obtained according to the first aspect 415 of the workflow shown in FIG. 4.

Electronic apparatus 565 (e.g., electromagnetic sensors, current sensors, etc.) can be used in conjunction with the controller 525 to perform tasks associated with taking measurements downhole. The communications unit 540 can include downhole communications in a drilling operation. Such downhole communications can include a telemetry system.

The system 500 can also include a bus 527 to provide common electrical signal paths between the components of the system 500. The bus 527 can include an address bus, a data bus, and a control bus, each independently configured. The bus 527 can also use common conductive lines for providing one or more of address, data, or control, the use of which can be regulated by the controller 525.

The bus 527 can include instrumentality for a communication network. The bus 527 can be configured such that the components of the logging system 500 are distributed. Such distribution can be arranged between downhole components such as the measurement device 504 and components that can be disposed on the surface of a well. Alternatively, several of these components can be co-located, such as on one or more collars of a drill string or on a wireline structure.

In various embodiments, the system 500 includes peripheral devices that can include displays 555, additional storage memory, or other control devices that may operate in conjunction with the controller 525 or the processing unit 502. The display 555 can display diagnostic, measurement, and alarm information, based on the signals generated, received, and processed according to embodiments described above.

In an embodiment, the controller 525 can be fabricated to include one or more processors. The display 555 can be fabricated or programmed to operate with instructions stored in the processing unit 502 (for example in the memory 506) to implement a user interface to manage the operation of the system 500, as well as components distributed within the system 500. This type of user interface can be operated in conjunction with the communications unit 540 and the bus 527. Various components of the logging system 500 can be integrated with the NMR transmitters receivers 506 and the housing 510, such that processing identical to or similar to the methods discussed previously, and those that follow, can be accomplished with respect to various embodiments that are described herein.

In various embodiments, a non-transitory machine-readable storage device may comprise instructions stored thereon, which, when performed by a machine, cause the machine to become a customized, particular machine that performs operations comprising one or more features similar to or identical to those described with respect to the methods and techniques described herein. A machine-readable storage device, herein, is a physical device that stores information (e.g., instructions, data), which when stored, alters the physical structure of the device. Examples of machine-readable storage devices can include, but are not limited to, memory 306 in the form of read only memory (ROM), random access memory (RAM), a magnetic disk storage device, an optical storage device, a flash memory, and other electronic, magnetic, or optical memory devices, including combinations thereof.

The physical structure of stored instructions may be operated on by one or more processors such as, for example, the processing unit 502. Operating on these physical structures can cause the machine to become a specialized machine that performs operations according to methods described herein. The instructions can include instructions to cause the processing unit 502 to store associated data or other data in the memory 506. The memory 506 can store the results of measurements of formation and casing/tubing parameters, to include gain parameters, calibration constants, identification data, sensor location information, etc.

The memory 506 can store a log of the measurement and location information provided by the measurement device 504. The memory 506 therefore may include a database, for example a relational database. In some embodiments, the database may comprise the correlation of $T_1/T_2$ ratios, TE values, and viscosity established in the first aspect of the method 411 shown in FIG. 4.

Figure 6:
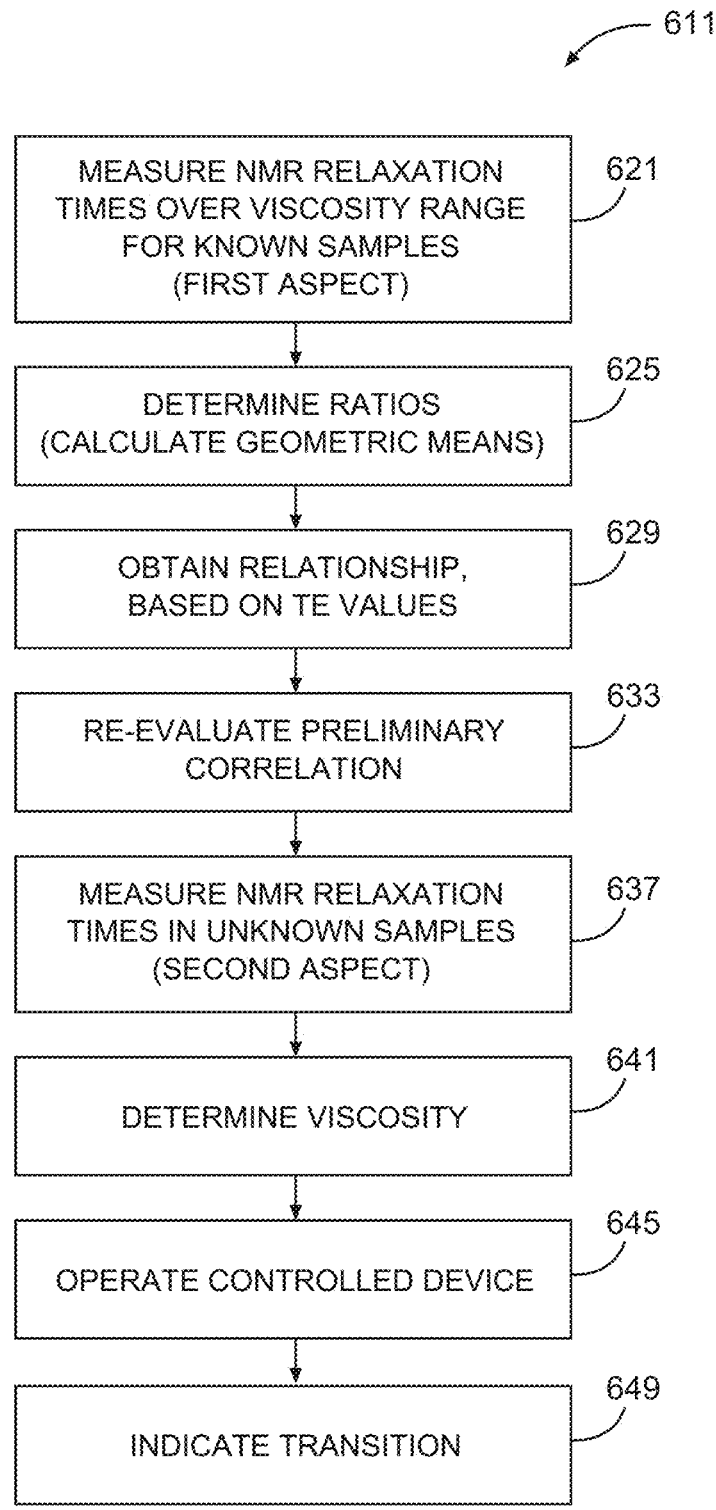
FIG. 6 is a method flow diagram, according to various embodiments.

FIG. 6 is a method 611 flow diagram, according to various embodiments. The activities accomplished in the method 611 described herein are with reference to the method of FIG. 4, and the apparatus and systems shown in FIGS. 5 and 7-8. Many variations may be realized.

For example, in some embodiments, a first aspect of the method 611 operates to establish a correlation between heavy oil viscosity and values of the NMR $T_1/T_2$ ratio in a first aspect, where the established correlation can be applied to determine the viscosity of oil in an unknown well, as part of a second aspect of the method 611. Activities that form part of the method 611 might therefore include building a lookup table via sampling the NMR response of oils over a range of viscosity values to determine a correlation between the viscosity and the relaxation time ratio of $T_1/T_2$.

Thus, in some embodiments, a first aspect of the method 611 begins at block 621 with measuring NMR relaxation times in a plurality of fluids associated with a plurality of viscosity values. These measurements may be conducted using a quantity of fluids (e.g., oils) having known values of viscosity. In most embodiments, these measurements of relaxation times further comprise measuring the relaxation times over a range of echo spacing times (TE).

Relaxation times can be measured in various ways. For example, $T_1$ can be measured via inversion recovery or saturation recovery. $T_2$ can be measured using the Car-Purcel-Meiboom-Gill (CPMG) echo train. Thus, in some embodiments, measuring the relaxation times further comprises determining inversion recovery or saturation recovery in the fluid.

Excitation can be accomplished using different activation sequences, according to expected viscosity. For example, if light oil is expected, longer wait times can be used. For heavy oil, shorter wait times can be used. Thus, in some embodiments, the activity at block 621 may comprise exciting the fluid with an NMR activation sequence based on an expected value of the viscosity.

The geometric mean of relaxation time groups can be determined to offset the broad distribution of relaxation times for heavy oils. Thus, in some embodiments, the method 611 may continue on to block 625 to comprise calculating geometric means of the distributions of the relaxation times. The activity at block 625 may further include determining the relaxation time ratios using the values of the geometric means that have been calculated. The relaxation time ratios can include ratios of $T_1/T_2$ (spin-lattice relaxation time/spin-spin relaxation time).

Relaxation time measurements can be verified by making the measurements over a range of echo spacing time values. Thus, as part of determining viscosity in some embodiments, the method 611 includes, at block 629, determining the relaxation times associated with a range of echo spacing times (TE).

At this point, the method 611 may include, at block 629, using regression analysis to obtain a relationship between ratios of the nuclear magnetic resonance relaxation times and the plurality of viscosity values, based on echo spacing time.

The correlation can be established using a specific form, with fitting coefficients. Thus, in some embodiments, the activity at block 629 may comprise establishing a preliminary correlation prediction is determined according to $\eta=(aTE+c)(T_1/T_2)+b$, where $\eta$ is the viscosity, TE is an echo spacing time within the range of echo spacing time values, $T_1$ and $T_2$ are members of the relaxation times, and a, b, c are fitting coefficients.

The preliminary viscosity correlation relationship can be re-evaluated over a range of echo spacing times. Thus, in some embodiments of the method 611, determining the measured viscosity includes, at block 633, re-evaluating the preliminary correlation prediction, based on the relationship, over the range of TE values.

The outcome of multiple NMR measurements can be averaged over a range of echo spacing time (TE) values. Thus, in some embodiments, re-evaluating the preliminary correlation prediction at block 633 further comprises averaging multiple ratios of relaxation times.

In a second aspect of the method 611, the established correlation is applied to lab or field measurement data (e.g., NMR core or log data) to determine the viscosity in a sample, well, or reservoir of interest. Thus, in some embodiments, the method 611 comprises measuring NMR relaxation times at block 637, determining viscosity based on ratios of the relaxation times at block 641, and operating a device according to the determined viscosity at block 645.

The relaxation times can be measured in a bulk fluid, or in fluid in the pore space of a reservoir rock formation. The measurements can be made during logging operations, and during other operations. NMR measurements of heavy oil viscosity are useful in many embodiments because they can be accomplished in situ (e.g., while the fluid is still located inside rock), avoiding potential formation damage due to pumping. For example, a heavy oil reservoir may comprise an unconsolidated sand formation, which may be vulnerable to pumping damage. In addition, fluid extracted and measured ex situ may not contain whole fluid components. This includes the heavy asphaltene component that is present in some oils, which may be precipitated, and thus absent from the extracted fluid—which affects the accuracy of the determined viscosity.

Thus, in a second aspect of some embodiments of the method 611, measuring NMR relaxation times in a fluid is included at block 637. This activity may further comprise measuring the NMR relaxation times in an unknown fluid located in situ, in a pore space of a geological formation.

In some embodiments, the method 611 may thus continue on to block 641 to include determining a viscosity of the fluid based on at least one ratio (i.e., one or more ratios) of the relaxation times. This activity may include, for example, determining the measured viscosity of the unknown fluid (e.g., located in situ, in a pore space of a geological formation), based on the relationship determined in the first aspect of the method 611.

In some embodiments, viscosity of an unknown fluid can be determined by accessing a lookup table, which includes information similar to what is shown in FIG. 2. Thus, the activity of determining the viscosity of the unknown fluid at block 641 may comprise accessing a lookup table of stored viscosity correlation data.

The method 611 may continue on to block 645 to include operating a controlled device based on the determined viscosity. For example, the determined viscosity can be used to control the operation of a pump, such as a pump used to extract hydrocarbons from a borehole. Therefore, operating the controlled device at block 645 may comprise controlling a pump according to the viscosity.

Values of the viscosity can be published to a printout or a display, among others. Thus, operating the controlled device at block 645 may comprise publishing a value of the viscosity in a human-readable form.

Users can be alerted when the viscosity enters a desired range, or leaves the desired range. This alert can happen during logging activities, pumping activities, etc. Even when it is known that heavy oil is present in the well, prior to well logging or pumping, changes in the quantitative value can be monitored. This can be accomplished during NMR logging operations, and during other operations. Thus, the activity at block 645 may comprise triggering an audio or visual indication when the viscosity is within a selected range.

Similarly, the transition between light and heavy oil can be roughly distinguished once the ratio of $T_1/T_2$ is greater than a value of about one. Thus, the method 611 may comprise, at block 649, indicating a transition from light oil to heavy oil based on at least one ratio of relaxation times. Many other embodiments may be realized.

It should be noted that the methods described herein do not have to be executed in the order described, or in any particular order. Moreover, various activities described with respect to the methods identified herein can be executed in iterative, serial, or parallel fashion. Information, including parameters, commands, operands, and other data, can be sent and received in the form of one or more carrier waves.

Upon reading and comprehending the content of this disclosure, one of ordinary skill in the art will understand the manner in which a software program can be launched from a computer-readable medium in a computer-based system to execute the functions defined in the software program, to perform the methods described herein. One of ordinary skill in the art will further understand the various programming languages that may be employed to create one or more software programs designed to implement and perform the methods disclosed herein. For example, the programs may be structured in an object-orientated format using an object-oriented language such as Java or C#. In another example, the programs can be structured in a procedure-orientated format using a procedural language, such as assembly or C. The software components may communicate using any of a number of mechanisms well known to those of ordinary skill in the art, such as application program interfaces or inter-process communication techniques, including remote procedure calls. The teachings of various embodiments are not limited to any particular programming language or environment. Thus, other embodiments may be realized.

Figure 7:
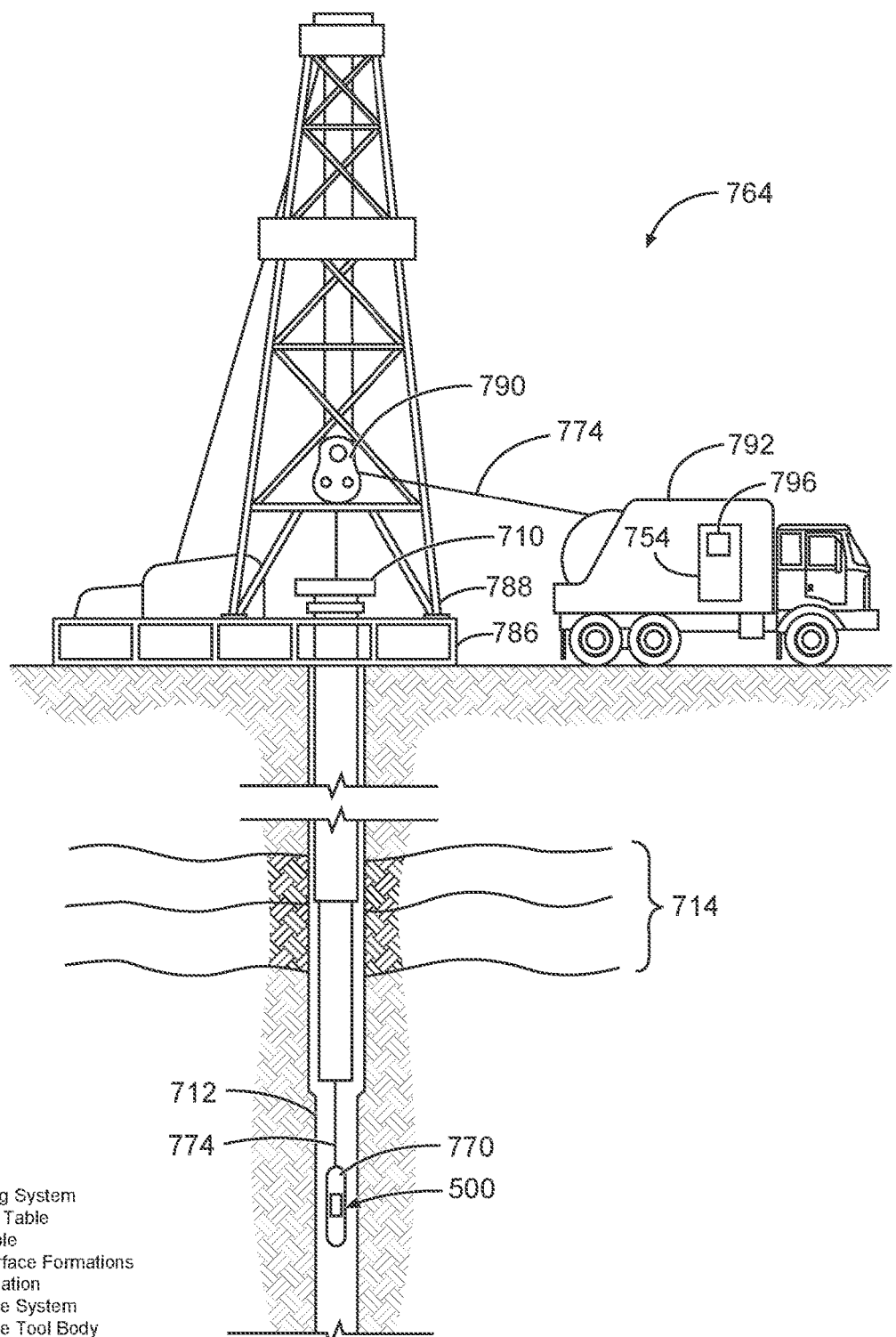
FIG. 7 depicts an example wireline system, according to various embodiments.
Figure 8:
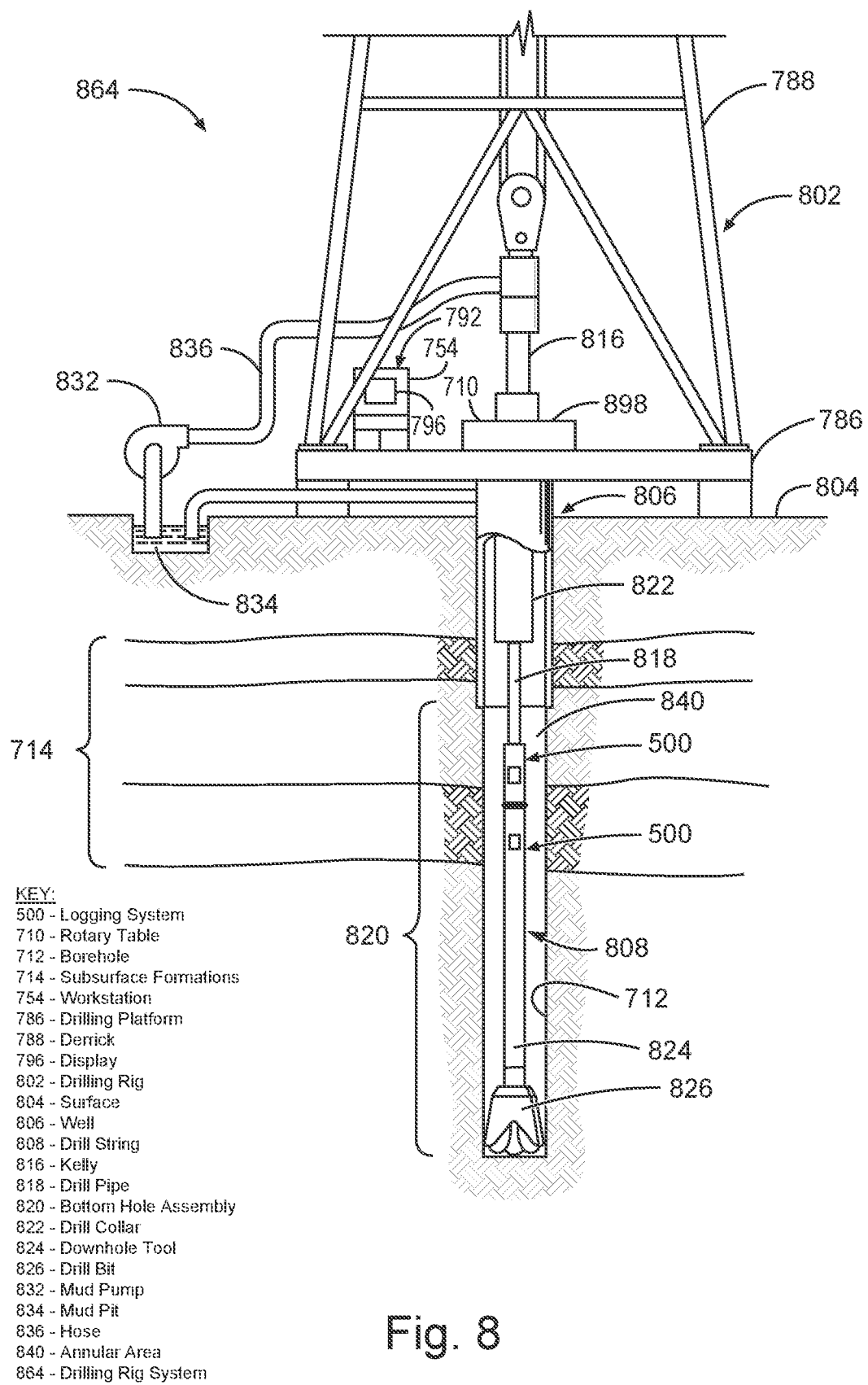
FIG. 8 depicts an example drilling rig system, according to various embodiments.

For example, FIG. 7 depicts an example wireline system 764, according to various embodiments. FIG. 8 depicts an example drilling rig system 864, according to various embodiments. Either of the systems in FIG. 7 and FIG. 8 are operable to control a system 500, or any combination of its components (see FIG. 5), perhaps mounted to a wireline logging body 770, or a downhole tool 824; to conduct measurement operations in a well, to determine viscosity conditions, and to control devices as part of hydrocarbon exploration and recovery operations. Thus, the systems 764, 864 may comprise portions of a wireline logging tool body 770 as part of a wireline logging operation, or of a downhole tool 824 (e.g., a drilling operations tool) as part of a downhole drilling operation.

Returning now to FIG. 7, a well during wireline logging operations can be seen. In this case, a drilling platform 786 is equipped with a derrick 788 that supports a hoist 790.

Drilling oil and gas wells is commonly carried out using a string of drill pipes connected together so as to form a drilling string that is lowered through a rotary table 710 into a well, also called a borehole 712. Here it is assumed that the drilling string has been temporarily removed from the borehole 712 to allow a wireline logging tool body 770, such as a probe or sonde, to be lowered by wireline or logging cable 774 into the borehole 712. Typically, the wireline logging tool body 770 is lowered to the bottom of the region of interest and subsequently pulled upward at a substantially constant speed.

During the upward trip, at a series of depths the instruments (e.g., the measurement device 504 shown in FIG. 11) included in the tool body 770 may be used to perform measurements on the subsurface geological formations adjacent the borehole 712 (and the tool body 770). The measurement data can be communicated to a surface logging facility 792 for storage, processing, and analysis. The logging facility 792 may be provided with electronic equipment for various types of signal processing, which may be implemented by any one or more of the components of the system 500 shown in FIG. 5. Similar formation evaluation data may be gathered and analyzed during drilling operations (e.g., during LWD operations, and by extension, sampling while drilling).

In some embodiments, the tool body 770 comprises one or more systems 500 for obtaining and communicating measurements in a subterranean formation through a borehole 712. The tool is suspended in the well by a wireline cable 774 that connects the tool to a surface control unit (e.g., comprising a workstation 754, which can also include a display 796). The tool may be deployed in the borehole 712 on coiled tubing, jointed drill pipe, hard wired drill pipe, or any other suitable deployment technique.

Turning now to FIG. 8, it can be seen how a system 864 may also form a portion of a drilling rig 802 located at the surface 804 of a well 806. The drilling rig 802 may provide support for a drill string 808. The drill string 808 may operate to penetrate the rotary table 710 for drilling the borehole 712 through the subsurface formations 714. The drill string 808 may include a Kelly 816, drill pipe 818, and a bottom hole assembly 820, perhaps located at the lower portion of the drill pipe 818.

The bottom hole assembly 820 may include drill collars 822, a downhole tool 824, and a drill bit 826. The drill bit 826 may operate to create the borehole 712 by penetrating the surface 804 and the subsurface formations 814. The downhole tool 824 may comprise any of a number of different types of tools including MWD tools, LWD tools, and others.

During drilling operations, the drill string 808 (perhaps including the Kelly 816, the drill pipe 818, and the bottom hole assembly 820) may be rotated by the rotary table 710. Although not shown, in addition to, or alternatively, the bottom hole assembly 820 may also be rotated by a motor (e.g., a mud motor) that is located downhole. The drill collars 822 may be used to add weight to the drill bit 826. The drill collars 822 may also operate to stiffen the bottom hole assembly 820, allowing the bottom hole assembly 820 to transfer the added weight to the drill bit 826, and in turn, to assist the drill bit 826 in penetrating the surface 804 and subsurface formations 714.

During drilling operations, a mud pump 832 may pump drilling fluid (sometimes known by those of ordinary skill in the art as "drilling mud") from a mud pit 834 through a hose 836 into the drill pipe 818 and down to the drill bit 826. The drilling fluid can flow out from the drill bit 826 and be returned to the surface 804 through an annular area 840 between the drill pipe 818 and the sides of the borehole 712. The drilling fluid may then be returned to the mud pit 834, where such fluid is filtered. In some embodiments, the drilling fluid can be used to cool the drill bit 826, as well as to provide lubrication for the drill bit 826 during drilling operations. Additionally, the drilling fluid may be used to remove subsurface formation cuttings created by operating the drill bit 826.

Thus, it may be seen that in some embodiments, the systems 764, 864 may include a drill collar 822, a downhole tool 824, and/or a wireline logging tool body 770 to house one or more systems 500, or components of the system 500, similar to or identical to those that have been described above.

Thus, for the purposes of this document, the term "housing" may include any one or more of a drill collar 822, a downhole tool 824, or a wireline logging tool body 770 (all having an outer wall, to enclose or attach to magnetometers, sensors, fluid sampling devices, pressure measurement devices, transmitters, receivers, fiber optic cable, acquisition and processing logic, and data acquisition systems). The tool 824 may comprise a downhole tool, such as an LWD tool or MWD tool. The wireline tool body 770 may comprise a wireline lagging tool, including a probe or sonde, for example, coupled to a logging cable 774. Many embodiments may thus be realized.

Any of the above components, including those of the systems 500, 764, 864 may all be characterized as "modules" herein. Such modules may include hardware circuitry, and/or a processor and/or memory circuits, software program modules and objects, and/or firmware, and combinations thereof, as desired by the architect of the apparatus and systems described herein, and as appropriate for particular implementations of various embodiments. For example, in some embodiments, such modules may be included in an apparatus and/or system operation simulation package, such as a software electrical signal simulation package, a power usage and distribution simulation package, a power heat dissipation simulation package, a measured radiation simulation package, a strain simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of apparatus and systems are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules. Thus, many other embodiments may be realized.

For example, referring now to FIGS. 5 and 7-8, it can be seen that in some embodiments, a system 500 may comprise a sensor (e.g., the receiver forming part of the NMR transmitter/receiver 506), and a processing unit 502, to measure relaxation times, and determine fluid viscosity.

In some embodiments, the system 500 comprises at least one sensor (e.g., as part of the device 504) to measure NMR relaxation times in a fluid. The system 500 may further comprise a processing unit 502 coupled to the at least one sensor to receive the relaxation times, where the processing unit can operate to determine the viscosity of the fluid based on at least one ratio of the relaxation times.

The sensor and processing unit may be housed by a downhole tool. Thus, in some embodiments, the at least one sensor (e.g., as part of the device 504, or NMR transmitter receiver 506, or apparatus 565) and the processing unit 702 are attached to a downhole tool that forms the housing 510.

The determined viscosity can be used to control a pump. Thus, the system 500 may comprise a pump (e.g., as a form of the controlled device 570) that is controlled to operate in response to the viscosity determined by the processing unit 502, to control a rate of hydrocarbon extraction from a geological formation.

When the viscosity rises above a desired value, an alarm can be used to indicate that condition. Thus, in some embodiments, the system 500 comprises an alarm (e.g., as a form of the controlled device 570) to indicate values of the viscosity above a selected threshold.

Transitions between ranges of viscosity can be monitored, and indicated. Thus, in some embodiments, the system 500 comprises a monitor MONITOR to indicate transitions between selected ranges of the viscosity.

In summary, using the apparatus, systems, and methods disclosed herein may provide the ability to use measurements of $T_1/T_2$ and TE to correct for the relaxation deficit due to tool limitations, which can be useful in the prediction of heavy oil viscosity. In addition, various embodiments permit the determination of formation fluid viscosity in situ, using log data, without the need for downhole sampling and additional outsourcing to labs for viscosity measurement. These advantages can significantly enhance the value of the services provided by an operation/exploration company, helping to reduce time-related costs, and providing greater return on investment.

Many other embodiments may be realized. Some of these will now be listed as non-limiting examples.

In some embodiments, a method comprises measuring nuclear magnetic resonance relaxation times in a fluid; determining a viscosity of the fluid based on at least one ratio of the relaxation times; and operating a controlled device based on the viscosity. Some embodiments include exciting the fluid with an NMR activation sequence based on an expected value of the viscosity. In some embodiments, measuring the nuclear magnetic resonance relaxation times in the fluid further comprises measuring nuclear magnetic resonance relaxation times in the fluid located in situ, in a pore space of a geological formation.

In some embodiments, the ratio(s) comprise ratio(s) of spin-lattice relaxation time and spin-spin relaxation time. Some embodiments include indicating a transition from light oil to heavy oil based on the ratio(s).

In some embodiments, operating the controlled device further comprises controlling a pump according to the viscosity. In some embodiments, operating the controlled device comprises publishing a value of the viscosity in a human-readable form. In some embodiments, operating the controlled device further comprises triggering an audio or visual indication when the viscosity is within a selected range.

In some embodiments, determining the viscosity further comprises determining the relaxation times associated with a range of echo spacing times.

In some embodiments, determining the viscosity further comprises accessing a lookup table of stored viscosity correlation data.

In some embodiments, measuring the relaxation times further comprises determining inversion recovery or saturation recovery in the fluid.

In some embodiments, a method comprises measuring nuclear magnetic resonance relaxation times in a plurality of fluids associated with a plurality of viscosity values; using regression analysis to obtain a relationship between ratios of the nuclear magnetic resonance relaxation times and the plurality of viscosity values, based on echo spacing time; and determining a measured viscosity of an unknown fluid located in situ, in a pore space of a geological formation, based on the relationship.

In some embodiments, a method comprises calculating geometric means of distributions of the relaxation times; and determining the ratio(s) using the geometric means.

In some embodiments, measuring the relaxation times further comprises measuring the relaxation times over a range of the echo spacing time, and determining the measured viscosity further comprises re-evaluating a preliminary correlation prediction, based on the relationship, over the range.

In some embodiments, the preliminary correlation prediction is determined according to $\eta=(aTE+c)(T_1/T_2)+b$, where $\eta$ is the viscosity, TE is an echo spacing time within the range of echo spacing time values, $T_1$ and $T_2$ are members of the relaxation times, and a, b, c are fitting coefficients.

In some embodiments, re-evaluating the preliminary correlation prediction further comprises averaging multiple ones of the ratios.

In some embodiments, a system comprises one or more sensors to measure nuclear magnetic resonance relaxation times in a fluid; and a processing unit coupled to the at least one sensor to receive the relaxation times, the processing unit to determine a viscosity of the fluid based on at least one ratio of the relaxation times.

In some embodiments of the system, the one or more sensors, and the processing unit are attached to a downhole tool.

In some embodiments, the system further comprises a pump controlled to operate in response to the viscosity determined by the processing unit, to control a rate of hydrocarbon extraction from a geological formation.

In some embodiments, the system further comprises an alarm to indicate values of the viscosity above a selected threshold.

In some embodiments, the system further comprises a monitor to indicate transitions between selected ranges of the viscosity. Many other embodiments may be realized.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of ordinary skill in the art upon reviewing the above description.

Although specific embodiments have been illustrated and described herein, it will be appreciated by those of ordinary skill in the art that any arrangement that is calculated to achieve the same purpose may be substituted for the specific embodiments shown. Various embodiments use permutations or combinations of embodiments described herein. It is to be understood that the above description is intended to be illustrative, and not restrictive, and that the phraseology or terminology employed herein is for the purpose of description. Combinations of the above embodiments and other embodiments will be apparent to those of ordinary skill in the art upon studying the above description.

What is claimed is:

1. An NMR viscosity pump controlling method, comprising:
   measuring, with an NMR transmitter/receiver, nuclear magnetic resonance (NMR) relaxation times in a fluid;
   determining, with a processing unit, a viscosity of the fluid based on at least one ratio of the measured relaxation times by comparing the at least one ratio of the measured relaxation times to reference ratios of relaxation times correlated to reference viscosity values for a plurality of distinct echo spacing times;
   using regression analysis to obtain at least one relationship between the at least one ratio of the measured NMR relaxation times, to reference ratios of NMR relaxation times correlated to the reference viscosity values for a plurality of distinct echo spacing times; and
   operating a controlled pump device according to and in response to the viscosity determined.

2. The NMR viscosity pump controlling method according to claim 1, further comprising: exciting the fluid with an NMR activation sequence based on an expected value of the viscosity.

3. The NMR viscosity pump controlling method according to claim 1, further comprising:
   operating the controlled pump device by publishing a value of the determined viscosity in a human-readable form, for human-operators to utilize in operating the controlled pump device.

4. The NMR viscosity pump controlling method according to claim 1, wherein the at least one ratio of the measured NMR relaxation times comprises a ratio of spin-lattice relaxation time and spin-spin relaxation time and where the value of the at least one ratio of the measured NMR relaxation times is a value above 2.

5. The NMR viscosity pump controlling method according to claim 1, wherein measuring the NMR relaxation times in the fluid further comprises: measuring NMR relaxation times in the fluid located in situ, in a pore space of a geological formation.

6. The NMR viscosity pump controlling method according to claim 1, further comprising: operating the controlled device by triggering an audio or visual indication when the determined viscosity is within a selected range.

7. The NMR viscosity pump controlling method according to claim 1, wherein determining the viscosity further comprises: the processing unit accessing a lookup table of stored viscosity correlation data.

8. The NMR viscosity pump controlling method according to claim 1, wherein measuring the NMR relaxation times further comprises: the processing unit determining inversion recovery or saturation recovery times within the fluid.

9. The NMR viscosity pump controlling method according to claim 1, further comprising: the processing unit indicating a transition from light oil to heavy oil based on the at least one ratio of the measured NMR relaxation times.

10. A NMR viscosity pump controlling method, comprising:
    controlling a pump that operates in response to a viscosity determined by a processing unit, in order to control a rate of hydrocarbon extraction from a geological formation;
    measuring, with an NMR transmitter/receiver, reference nuclear magnetic resonance (NMR) relaxation times associated with at least one reference echo spacing time in a plurality of reference fluids associated with a plurality of reference viscosity values;
    using regression analysis with the processing unit, in order to obtain at least one relationship between at least one ratio of the measured reference NMR relaxation times, along with the plurality of reference viscosity values and the at least one echo spacing time;
    determining with the processing unit, a measured viscosity of an unknown fluid located in situ, in a pore space of a geological formation, based on the at least one relationship from the utilized regression analysis, by applying the at least one relationship from the utilized regression analysis, to measurements of NMR relaxation times associated with at least one measured echo spacing time in the unknown fluid; and
    publishing the measured viscosity of the unknown fluid in a human readable form to a display or printout.

11. The NMR viscosity pump controlling method according to claim 10, further comprising: calculating with the processing unit, a geometric means of a distribution of the NMR relaxation times; and determining with the processing unit, at least one ratio of the measured reference NMR relaxation times using the calculated geometric means.

12. The NMR viscosity pump controlling method according to claim 10, wherein measuring the reference NMR relaxation times further comprises measuring the reference NMR relaxation times over a range of echo spacing times, and wherein determining the measured viscosity further comprises re-evaluating a preliminary correlation prediction, based on the obtained at least one relationship, over the range of echo spacing times.

13. The NMR viscosity pump controlling method according to claim 12, wherein the preliminary correlation prediction is determined according to $\eta=(aTE+c)(T_1/T_2)+b$, where $\eta$ is the viscosity, TE is an echo spacing time within the range of echo spacing time, $T_1$ and $T_2$ are the types of NMR relaxation times, and a, b, c are fitting coefficients.

14. The NMR viscosity pump controlling method according to claim 12, wherein the at least one ratio of the measured reference NMR relaxation times comprises multiple ratios of the measured reference NMR relaxation times, and wherein re-evaluating the preliminary correlation prediction further comprises: averaging the multiple ratios of the measured reference NMR relaxation times with the processing unit.

15. The method according to claim 10, further comprising:

using regression analysis with the processing unit, in order to obtain a different relationship between at least one ratio of the measured reference NMR relaxation times and the plurality of reference viscosity values for each of a plurality different echo spacing times; and determining with the processing unit, the measured viscosity of the unknown fluid by applying the different relationship for the echo spacing time of the measured echo spacing time in the unknown fluid.

16. An NMR viscosity pump controlling system, comprising:
   at least one sensor configured to measure nuclear magnetic resonance (NMR) relaxation times in a fluid;
   a processing unit coupled to the at least one sensor that is configured to receive the NMR relaxation times, with the processing unit being configured to determine a viscosity of the fluid from both at least one ratio of the NMR relaxation times and an echo spacing time associated with the NMR relaxation times,
   wherein the processing unit determines the viscosity by either:
      applying a predetermined relationship to the at least one ratio of the NMR relaxation times and the echo spacing time associated with the NMR relaxation times, the predetermined relationship established between known viscosity values of a reference fluid and ratios of measurement ratios of NMR relaxation times in the reference fluid with the echo spacing time associated therewith; and/or
      by comparing the at least one ratio of the NMR relaxation times and the echo spacing time to reference ratios of NMR relaxation times correlated to reference viscosity values for a plurality of echo spacing times; and
   a controlled pump device coupled to the processing unit, where the controlled pump device is operable based on whether the viscosity determined by the processing unit is above a selected threshold.

17. The NMR viscosity pump controlling system according to claim 16, wherein the at least one sensor and the processing unit are attached to a downhole tool.

18. The NMR viscosity pump controlling system according to claim 16, further comprising an alarm configured to indicate values of the determined viscosity above a selected threshold.

19. The NMR viscosity pump controlling system according to claim 16, further comprising: a monitor configured to indicate transitions between selected ranges of the determined viscosity.

* * * * *

UNITED STATES PATENT AND TRADEMARK OFFICE
CERTIFICATE OF CORRECTION

PATENT NO. : 10,353,032 B2
APPLICATION NO. : 15/516652
DATED : July 16, 2019
INVENTOR(S) : Magdalena Traico Sandor and Songhua Chen Page 1 of 1

It is certified that error appears in the above-identified patent and that said Letters Patent is hereby corrected as shown below:

In the Specification

Column 10, Line 22 change "lagging" to -- logging --

Signed and Sealed this
Eighteenth Day of February, 2020

Andrei Iancu
*Director of the United States Patent and Trademark Office*